United States Patent [19]

Amkraut et al.

[11] Patent Number: 5,702,727
[45] Date of Patent: Dec. 30, 1997

[54] COMPOSITIONS AND METHODS FOR THE ORAL DELIVERY OF ACTIVE AGENTS

[75] Inventors: Alfred A. Amkraut; Heechung Yang, both of Palo Alto, Calif.

[73] Assignee: Alza Corporation, Palo Alto, Calif.

[21] Appl. No.: 409,613

[22] Filed: Mar. 6, 1995

Related U.S. Application Data

[63] Continuation of Ser. No. 20,481, Feb. 22, 1993, abandoned.
[51] Int. Cl.⁶ .............................. A61K 9/14; A61K 9/51; A61K 9/64; A61K 38/00
[52] U.S. Cl. .................. 424/491; 424/489; 424/490; 428/402; 514/2; 514/773
[58] Field of Search ........................ 424/489, 490, 424/491; 514/2, 773

[56] References Cited

U.S. PATENT DOCUMENTS

| | | | |
|---|---|---|---|
| 3,845,770 | 11/1974 | Theeuwes et al. | 128/260 |
| 3,995,631 | 12/1976 | Higuchi et al. | 128/260 |
| 4,034,756 | 7/1977 | Higuchi et al. | 128/260 |
| 4,111,202 | 9/1978 | Theeuwes | 128/260 |
| 4,320,759 | 3/1982 | Theeuwes | 128/260 |
| 4,449,983 | 5/1984 | Cortese et al. | 604/892 |
| 4,925,678 | 5/1990 | Ranney | 424/493 |

FOREIGN PATENT DOCUMENTS

| | | | |
|---|---|---|---|
| 88351056 | 10/1931 | WIPO . | |
| WO9211846 | 7/1992 | WIPO . | |
| WO9214446 | 9/1992 | WIPO . | |
| WO9217167 | 10/1992 | WIPO | A61K 47/24 |

OTHER PUBLICATIONS

Michel, et al., J. Pharm. Pharmacol., Jan. 1991, 43:1–5, "The Effect of Site of Administration in the Gastrointestinal Tract on the Absorption of Insulin from Nanocapsules in Diabetic Rats".

Damgé, et al., Diabetes, vol. 37, pp. 246–251 Feb. (1988), "New Approach for Oral Administration of Insulin with Polyalkylcyanoacrylate Nano Capsules as Drug Carrier".

Dougan, et al., Biochemical Society Transactions, vol. 18, pp. 746–748, Apr. (1990), "Bacterial pathogens—a route to oral drug delivery".

Ruoslahti, et al., Science, vol. 238, pp. 491–497 Oct. (1987), "New Perspectivess in Cell Adhesion: RGD and Integrins".

Mueller, et al., The Journal of Cell Biology, vol. 109, pp. 3455–3464 Jan. (1989), "Dynamic Cytoskeleton–Integrin Associations Induced by Cell Binding to Immobilized Fibronectin".

Isberg, Molecular Microbiology, Mar. (1989) 3(10), 1449–1453, "Mammalian Cell Adhesion Functions and Cellular Penetration of Enteropathogenic Yersinia Species".

Isberg, Mol. Biol. Med., 7:73–82 Jan. (1990), "Pathways for the Penetration of Enteroinvasive Yersinia into Mammalian Cells".

Isberg, Ralph R. and Leong, John M., Cell 60:861–871 Jan. (1990), "Invasin, a Protein that Promotes Bacterial Penetration into Mammalian Cells".

Leong, et al., Infection and Immunity, vol. 59, No. 10, pp. 3424–3433 Oct. (1991), "Mapping and Topographic Localization of Epitopes of the Yersinia pseudotuberculosis Invasin Protein".

McKeown, et al., Cell Tissue Res., Apr. (1990), pp. 523–530, "Role of the Cellular Attachment Domain of Fibronectin in the Phagocytosis of Beads by Human Gingival Fibroblasts in vitro".

Berger et al., Cancer Research, Mar. (1988) vol. 48, pp. 1238–1243, "Correlation of c–erbB–2 Gene Amplification and Protein Expression in Human Breast Carcinoma with Nodal Status and Nuclear Grading".

Al Khouri et al., International Journal of Pharmaceutics, vol. 28 Jan. (1986) pp. 125–132, "Development of a New Process for the Manufacture of Polyisobutylcyanoacrylate Nanocapsules".

Damagé et al., Journal of Controlled Release vol. 13, Jan. (1990) pp. 233–239, "Nanocapsules as Carriers for Oral Peptide Delivery".

Heller, Biomaterials Jan. (1980) vol. 1, p. 51. (This reference will be sent to you when received.)

Sidman, et al., J. Membrane Science Jun. (1980) vol. 1, p. 277. (This reference will be sent to you when received.)

Heller, J., "Controlled Release of Biologically Active Compounds From Bioerodible Polymers", Biomaterials, Jan 1980 1 (1) pp. 51–57.

Sidman, K.R., et al., Journal of Membrane Science 7 Jun. (1980) vol. 1, pp. 277–291, "Biodegradable, Implantable Sustained Release systems Based on Glutamic Acid Copolymers".

*Primary Examiner*—Thurman K. Page
*Assistant Examiner*—James M. Spear
*Attorney, Agent, or Firm*—Michael J. Rafa; Christopher P. Rogers; Steven F. Stone

[57] ABSTRACT

Compositions and methods for the oral administration of drugs and other active agents are provided. The compositions comprise an active agent carrier particle attached to a binding moiety which binds specifically to a target molecule present on the surface of a mammalian enterocyte. The binding moiety binds to the target molecule with a binding affinity or avidity sufficient to initiate endocytosis or phagocytosis of the particulate active agent carrier so that the carrier will be absorbed by the enterocyte. The active agent will then be released from the carrier to the host's systemic circulation. In this way, degradation of degradation-sensitive drugs, such as polypeptides, in the intestines can be avoided while absorption of proteins and polypeptides from the intestinal tract is increased.

5 Claims, No Drawings

COMPOSITIONS AND METHODS FOR THE ORAL DELIVERY OF ACTIVE AGENTS

This application is a continuation of application Ser. No.08/020,481, filed Feb. 22, 1993, abandoned and benefit of the filing date of said earlier filed application is claimed under 35 U.S.C. § 120.

FIELD OF THE INVENTION

The present invention relates generally to compositions and methods for the oral delivery of drugs and other active agents. More particularly, the present invention relates to compositions and methods for orally delivering active agents present in particulate carriers which are targeted to certain cell surface receptors present on the intestinal mucosa.

BACKGROUND OF THE INVENTION

Proteins and polypeptides are minimally absorbed from the adult mammalian intestinal tract. The oral delivery of protein and polypeptide drugs is further complicated by the presence of proteolytic digestive enzymes in the stomach and intestines. Unprotected proteins which are administered orally are largely degraded by such enzymes before they are able to pass through the enteric wall and enter blood circulation. While many of these proteins can be successfully delivered by intravascular or intramuscular injection, such delivery routes suffer from low patient acceptability, particularly when the drugs must be administered on a regular basis by self-injection. Control of the delivery rate and frequency by this route is, in most cases, only possible in a hospital setting.

In order to avoid the need for injection, many approaches for modifying and protecting protein drugs against proteolytic degradation have been proposed. Of particular interest to the present invention, it has been proposed that proteins be incorporated into polymeric particles which resist proteolytic degradation when passing through the stomach and intestines and which are sufficiently small to pass through the intestinal mucosa to effect systemic delivery. While promising, the use of such "nanoparticles" suffers from certain disadvantages. In fact, it has been shown by many authors and for particles of different compositions that only a small fraction is allowed to pass into the systemic circulation and that most nanoparticles are excreted. Thus, nanoparticle carriers per se do not significantly enhance the absorption of the drug.

For these reasons, it would be desirable to provide improved compositions and methods for the oral administration and systemic delivery of polypeptide drugs. It would be particularly desirable to provide improved compositions which, in addition to protecting the drug being delivered, are able to target the protected drug to the intestinal mucosa to enhance the delivery rate of the drug and increase the residence time of the drug and particular carrier in the intestines. It would be especially desirable to provide improved compositions exhibiting the ability to induce the uptake of the drug carrier into the mucosal cell to increase the amount of drug delivered across the intestinal mucosa.

The use of nanoparticles for the oral delivery of insulin is described in Michel et al. (1991) J. Pharm. Pharmacol. 43:1–5, and Damgé et al. (1988) Diabetes 37:246–251. Dougan et al. (1990) Biochem. Soc. Trans. 18:746–748 suggests that invasins "may prove to be useful tools for studying methods for introducing drugs into cells." Invasins are surface proteins present on certain pathogenic bacteria. Invasins bind to integrins present on epithelial and other cells, mediating entry of the bacteria into the cell. Integrins are adhesion receptors whose normal function is to bind to extracellular matrices, such as fibronectin. Fibronectin and other cellular matrices include conserved recognition sites, such as arginine-glycine-aspartic acid (RGD), which bind to cell surface integrins (Ruoslahti and Pierschbacher (1987) Science 238:491–497; and Mueller et al. (1989) J. Cell Biol. 109:3455–3464). The relationship between invasins and integrins is described in a number of references, including Isberg (1989) Mol. Microbiol. 3:1449–1453; Isberg (1990) Mol. Biol. Med. 7:73–82; Isberg and Leong (1990) Cell 60:861–871; and Leong et al. (1991) Infect. Immun. 59:3424–3433. Fibronectin-coated latex beads have been shown to be phagocytosed by cultured fibroblasts (McKeown et al. (1990) Cell Tissue Res. 523–530). Adhesion molecules derived from bacteria have been purified and attached to particles as a model for drugs having controlled transit time through the intestines (WO 90/04963); however, these adhesion molecules have not been shown to promote endocytosis or phagocytosis.

SUMMARY OF THE INVENTION

Compositions according to the present invention comprise a carrier particle attached to a binding moiety which binds to a target receptor (molecule) present on the surface of a mammalian enterocyte. The target receptor is selected from cell surface molecules which promote endocytosis or phagocytosis. The carrier particle comprises a protective matrix which is suitable for encapsulating or otherwise retaining (e.g. by absorption or dispersion) an active agent therein. Useful binding moieties are selected to specifically bind to enteric cell surface receptors which promote endocytosis or phagocytosis.

Pharmaceutical compositions according to the present invention comprise active agent-containing compositions as described above present in a pharmaceutically acceptable vehicle at a pharmaceutically effective concentration.

Methods for systemically delivering an active agent to a mammalian host according to the present invention comprise administering to the host a composition including an active agent present in a carrier particle attached to a binding moiety which binds specifically to an endocytosis- or phagocytosis-promoting target molecule present on the surface of a mammalian enterocyte. The carrier particle will be able to be absorbed by an enterocyte prior to release of the active agent from the particle. The methods are particularly useful for delivering drugs and other active agents which are sensitive to degradation in the intestines or are normally poorly absorbed in the intestine.

DESCRIPTION OF SPECIFIC EMBODIMENTS

The compositions and methods of the present invention are intended for targeted active agent delivery to and through the intestinal mucosa, where the active agents will be delivered into the patient's blood circulation at a relatively high rate with little or no proteolytic degradation from digestive enzymes. The active agents are present in carrier particles which are attached to binding moieties which recognize certain conserved receptors on the enterocytes which form the intestinal mucosa. The binding moieties are selected to bind with sufficient affinity or avidity to initiate endocytosis or phagocytosis of the agent carrier particle, so that the agent carrier particle will thus be absorbed by the enterocyte. The carrier may then be released from the basolateral surface of the cell into the patient's blood circulation where the active agent is then released from the carrier to the blood. Alternately, the active agent may be released from the carrier inside the enterocyte and then be secreted on the basolateral membrane of the cell to pass into the systemic circulation.

The terms "active agent" and "drug" are used interchangeably herein. The active agents that can be delivered according to the present invention include inorganic and organic drugs without limitation and include drugs that act on the peripheral nerves, adrenergic receptors, cholinergic receptors, nervous system, skeletal muscles, cardiovascular system, smooth muscles, blood circulatory system, synaptic sites, neuro-effector junctional sites, endocrine system, hormone systems, immunological system, reproductive system, skeletal system, autocoid systems, alimentary and excretory systems, histamine systems, and the like. The active drug that can be delivered for acting on these recipients includes, but is not limited to, anticonvulsants, analgesics, antiparkinsons, anti-inflammatories, calcium antagonists, anesthetics, antimicrobials, antimalarials, antiparasitics, antihypertensives, antihistamines, antipyretics, alpha-adrenergic agonists, alpha-blockers, biocides, bactericides, bronchial dilators, beta-adrenergic blocking drugs, contraceptives, cardiovascular drugs, calcium channel inhibitors, depressants, diagnostics, diuretics, electrolytes, enzymes, hypnotics, hormones, hypoglycemics, hyperglycemics, muscle contractants, muscle relaxants, neoplastics, glycoproteins, nucleoproteins, lipoproteins, ophthalmics, psychic energizers, sedatives, steroids, sympathomimetics, parasympathomimetics, tranquilizers, urinary tract drugs, vaccines, vaginal drugs, vitamins, nonsteroidal anti-inflammatory drugs, angiotensin converting enzymes, polynucleotides, polypeptides, polysaccharides, and the like.

The present invention is particularly suitable for delivering polypeptide drugs which are both poorly absorbed and subject to proteolytic degradation in the patient's intestines. Such polypeptide drugs can be any natural or synthetic polypeptide which may be orally administered to a mammalian host, usually a human patient. Exemplary drugs include, but are not limited to, insulin; growth factors, such as epidermal growth factor (EGF), insulin-like growth factor (IGF), transforming growth factor (TGF), nerve growth factor (NGF), platelet-derived growth factor (PDGF), bone morphogenic protein (BMP), fibroblast growth factor and the like; somatostatin; somatotropin; somatropin; somatrem; calcitonin; parathyroid hormone; colony stimulating factors (CSF); clotting factors; tumor necrosis factors; interferons; interleukins; gastrointestinal peptides, such as vasoactive intestinal peptide (VIP), cholecytokinin (CCK), gastrin, secretin, and the like; erythropoietins; growth hormone and GRF; vasopressins; octreotide; pancreatic enzymes; dismutases such as superoxide dismutase; thyrotropin releasing hormone (TRH); thyroid stimulating hormone; luteinizing hormone; LHRH; GHRH; tissue plasminogen activators; macrophage activator; chorionic gonadotropin; heparin; atrial natriuretic peptide; hemoglobin; retroviral vectors; relaxin; cyclosporin; oxytocin; vaccines; monoclonal antibodies; and the like; and analogs and derivatives of these compounds.

The active agent for delivery in this invention can be in various pharmaceutically acceptable forms, such as uncharged molecules, molecular complexes, and pharmacologically acceptable salts. For acidic medicines, salts of metals, amines or organic cations, for example quaternary ammonium, can be used. Derivatives of medicines, such as esters, ethers and amides, can be used.

The conserved receptors (target molecules) will usually be cell surface integrins or other endocytosis- or phagocytosis-promoting molecules which are naturally present on the cell surface of mammalian enterocytes which line the intestines. Integrins are heterodimeric glycoproteins consisting of approximately 115kD and 140–160kD subunits, being members of the VLA super family of receptors, as described generally in Hynes (1987) Cell 48:549–554, and Isberg (1990) Mol. Biol. Med. 7:73–82, the disclosures of which are incorporated herein by reference. Integrins act as receptors for various extracellular matrix proteins as described above. The exemplary integrins of the intestinal mucosa include a3b1, a4b1, a5b1, a6b1, and the like.

Alternate cell surface receptors which can act as target molecules include, but are not limited to, transferrin receptors, pseudomonas exotoxin receptors, vitamin D receptors, diphtheria toxin. receptors, cholera toxin receptors, epidermal growth factor (EGF) receptors, pIgA receptors, $F_c$ receptors, lactoferrin receptors, and receptors for viruses, e.g. adenovirus.

Suitable binding moieties will comprise chemical structures which are capable of binding to the target molecule(s) with sufficient affinity or avidity to initiate endocytosis or phagocytosis, as described above. By "affinity" it is meant that a single binding moiety will bind to a single target molecule with a minimum threshold binding constant, usually being above $10^{-5}$ M, more usually being above $10^{-6}$ M, and preferably being above 10–7 M. By "avidity," it is meant that two or more binding moieties present on a single drug carrier particle will bind to two or more separate target molecules on the enterocyte, where the individual binding interactions between binding moieties and target molecules contribute to an overall binding constant of at least $10^{-5}$ M, preferably being at least $10^{-6}$ M, and more preferably being $10^{-9}$ M or higher. It will be appreciated that the individual binding constants of each binding interaction may be lower than those set forth, but that taken into the aggregate, binding between the binding moiety and target molecule will preferably meet these threshold levels in order to promote the desired endocytosis or phagocytosis of the drug carrier particles by the enterocyte.

The binding moieties may be any small or large molecular structure which provides the desired binding interaction(s) with the cell surface receptors on the enterocytes. Conveniently, the binding moieties will comprise or mimic adhesion molecules present on a pathogen or an extracellular matrix molecule, where the adhesion molecule is a natural binding partner to the integrin or other cell surface receptor on a mammalian enterocyte. Such adhesion molecules are usually proteins or glycoproteins, and the binding moieties of the present invention are preferably fragments of such adhesion proteins which retain the natural binding activity. Such fragments will typically comprise 50 or fewer amino acids, preferably fewer than 25 amino acids, frequently containing as few as 10 amino acids, or below.

Exemplary adhesion molecules include invasin proteins of certain pathogenic bacteria, such as *Yersina*, *Shigella*, and *Salmonella*. Suitable invasins are encoded by the ail gene families of each of these species, as described in Leong et al. (1991) Infect. Immun. 59:3424–3433, the disclosure of which is incorporated herein by reference.

In addition to invasins, a suitable binding moiety may be, for example, a mono- or polyclonal antibody or fragment thereof, an IgA antibody or fragment thereof, a viral capsid, a capsid of adenovirus, cholera toxin B subunit, transferrin or a fragment thereof, lactoferrin or a fragment thereof, vitamin D, EGF or a fragment thereof, pseudomonas exotoxin, diphtheria toxin, and the like.

Additional suitable binding moieties may comprise or mimic natural adhesion to molecules present in the extracellular matrix, particularly in matrix proteins, such as fibronectin, collogan, laminin, proteoglycans, elastins, hyaluronic acids, fibrinogens, vitronectins, osteopontins, and the like, and fragments thereof.

Particularly preferred binding moieties will contain the tripeptide arginine-glycine-aspartic acid (RGD) or the pentapeptide glutamic acid-isoleucine-leucine-aspartic acid-valine (EILDV) within their binding recognition site. The RGD tripeptide is widely conserved among many adhesive proteins present in extracellular matrices as well as being part of at least most invasin proteins. The RGD peptide may be utilized by itself and bound to the drug carrier particle, as described in more detail hereinbelow, or it may be obtained or synthesized as part of a larger oligopeptide which is bound to the drug carrier particle. RGD peptide is commercially available from GIBCO BRL Life Technologies, Inc. (Gaithersburg, Md.) and as Peptite-2000™ from Telios. Additional preferred binding moieties are the peptides arginine-glycine-aspartic acid-valine (RGDV), arginine-glycine-aspartic acid-serine (RGDS), arginine-glycine-aspartic acid-phenylalanine (RGDF), and glycine-arginine-glycine-aspartic acid-threonine-proline (GRGDTP).

It will be appreciated that the binding moiety may comprise a variety of other molecular structures, including antibodies, lectins, nucleic acids, and other receptor ligands, and fragments thereof. Once a desired target molecule is known, such as the integrins identified above, it will be possible to prepare or synthesize other molecules which are capable of binding the target with the requisite affinity or avidity. For example, antibodies, including both polyclonal and monoclonal antibodies, may be raised against the integrin or other target molecule using conventional techniques, as described in Harlow and Lane, eds., *Antibodies: A Laboratory Manual*, Cold Spring Harbor Laboratory, Cold Spring Harbor, N.Y. (1988), the disclosure of which is incorporated herein by reference.

Additionally, it will be possible to design other non-protein compounds to be employed as the binding moiety, using techniques known to those working in the area of drug design. Such methods include, but are not limited to, self-consistent field (SCF) analysis, configuration interaction (CI) analysis, and normal mode dynamics computer programs, all of which are well described in the scientific literature. See Rein et al., *Computer-Assisted Modeling of Receptor-Ligand Interactions*, Alan Liss, N.Y. (1989). Preparation of non-protein compounds and moieties will depend on their structure and other characteristics and may normally be achieved by standard chemical synthesis techniques. See, for example, *Methods in Carbohydrate Chemistry*, Vols. I-VII; *Analysis and Preparation of Sugars*, Whistler et al., Eds., Academic Press, Inc., Orlando (1962), the disclosures of which are incorporated herein by reference.

The active agent carrier particle of the present invention comprises a protective matrix which encapsulates or otherwise retains (e.g. by absorption or dispersion) the drug therein. The structure of the protective matrix will be such that (i) the particle can be covalently or non-covalently attached to the binding moiety, as described below, (ii) the particle will protect the drug from degradation while present in the stomach and intestines, and (iii) the particle will release the drug at a desired time, after the particle has been absorbed by the enterocyte. The carrier particle will be composed of a material which resists proteolytic degradation. What is meant by the term "resists proteolytic degradation" as used herein is that the carrier particle does not degrade in the stomach and intestines or degrades to only a limited extent so that the active agent retained by or within the particle is protected from the adverse effects of intestinal enzymes. The carrier particle may comprise a variety of forms, including metal particles and sols, ceramic particles, protein structures, carbohydrate structures, and the like, but will preferably comprise organic polymers which have been synthesized to coat or contain the drug, e.g. by absorption or dispersion. Such coating methods, generally referred to as encapsulation, are well described in the scientific and patent literature. See, for example, Heller (1980) Biomaterials 1:51 and Sidman et al. (1980) J. Membrane Sci. 1:277, the disclosures of which are incorporated herein by reference. More preferably, the protective matrix will comprise a porous polymeric particle, such as a porous microbead or nanoparticle, into which the drug is dispersed or absorbed.

Particularly preferred porous nanoparticles are described in Michel et al. (1991) J. Pharmacol. 43:1–5 and Damgé et al. (1988) J. Diabetes 37:246–251, the disclosures of which are incorporated herein by reference. Such particles are prepared by interfacial emulsion polymerization of a suitable acrylate, such as isobutylcyanoacrylate, as described in Al Khouri et al. (1986) Int. J. Pharm. 28:125–132, the disclosure of which is incorporated herein by reference. Briefly, the active agent is added to a lipophilic phase containing a fatty acid, such as miglyol, and isobutyl-2-cyanoacrylate dissolved in inorganic solvent, such as ethanol. The lipophilic phase is added to an aqueous phase containing a non-ionic surfactant, and the nanoparticles are formed by agitation, such as mechanical stirring. The particle size will depend on the rate of agitation, the amount of added surfactant, and the like, and the resulting colloidal suspension may be concentrated by conventional means, such as evaporation, filtration, and the like.

The active agent may be absorbed or dispersed into or otherwise retained in or on the carrier particle either prior to or after the binding moiety or moieties have been coupled to the particle carrier.

The binding moiety or moieties may be attached to the particulate active agent carrier covalently or non-covalently, with covalent coupling being achieved directly or achieved indirectly through the use of a suitable linking region or group. Non-covalent binding may be achieved by utilizing strong ionic interactions, hydrophobic interactions, Van der Waals forces, and the like, between the binding moiety and the particle.

Direct covalent attachment between available binding functionalities on the particle and on the binding moiety may be achieved by conventional techniques relying on activation of either or both of the functionalities. See, for example, *Chemistry of Protein Conjugation and Crosslinking*, S. S. Wong (1991) CRC Press.

Preferably, covalent binding between the binding moiety and the carrier particle will be achieved using a bifunctional compound having a reactive group at one end which is capable of binding to the binding moiety and a second reactive group at the other end which is capable of binding to the carrier particle. Alternatively, a linking region may be synthesized together with the binding moiety which may then be directly coupled to the carrier particle, as described above.

The nature of the linking region is not critical, but it should provide a sufficient spacing and flexibility between the binding moiety and the carrier particle so that the binding moiety is available to interact with the target molecule on the enterocyte. The length of the linking region will typically be between about 5 Å and 100 Å, preferably being between about 10 Å and 20 Å. The linking region should itself be resistant to proteolytic degradation while present in the intestines and stomach and should, of course, be non-toxic.

Exemplary bifunctional compounds which can be used for attaching the binding moiety to the carrier particle are set forth in Table I as follows:

TABLE I

COVALENT COUPLING REAGENTS

1. For amino groups 1,5-difluoro-2,4-dinitrobenzene
p,p'-difluoro-m,m'-dinitrodiphenyl sulfone
dimethyl adipimidate
phenol-2,4-disulfonyl chloride
hexamethylenediisocyanate
glutaraldehyde
bis(N-hydroxysuccinimide) esters
bis(sulfo-N-hydroxysuccinimide) esters 2. For sulfyhydryl groups mercuric ion
3,6-bis(mercurimethyl)dioxane
N,N'-(1,3-phenylene)bismaleimide
N,N'-ethylene-bis(iodoacetamide)

3. For disulfide groups bis(thiols)

4. For coupling between amino and carboxyl groups carbodiimides
Woodward's reagent K 5. For coupling between amino and sulfhydryl groups succinimidyl maleimido compounds
succinimidyl iodoacetyl compounds 6. Photoreactive reagents bis(azido) compounds
azido succinimidyl compounds
4-azidophenyl glyoxal A preferred bifunctional compound for covalently coupling the RGD tripeptide to an active agent-encapsulated polyisobutylcyanoacrylate nanoparticle is selected from the water-soluble carbodiimides.

As another example of covalent attachment, EGF molecules are attached to the surface of a carboxylate-modified latex nanoparticle using, again, a carbodiimide coupling reagent. In this example, the active agent is adsorbed on the surface of the nanoparticles after covalent attachment of the EGF endocytosing ligands to the particles.

The particulate drug carrier particles of the present invention will include at least one binding moiety, and will frequently include two or more binding moieties, often having from $10^2$ to $10^5$ binding moieties. The presence of multiple binding moieties on the surface of each drug carrier particle will often provide multivalent binding to the enterocyte target molecules, increasing the binding avidity.

The compositions of the present invention will generally be formulated as pharmaceutical compositions where the binding moiety-derivatized active agent carrier particles are incorporated into pharmaceutically acceptable vehicles at pharmaceutically effective concentrations. By "pharmaceutically acceptable," it is meant that the vehicle will be suitable for oral administration to mammalian, and more particularly human hosts. Such vehicles are well known in the art, typically being a liquid vehicle, such as water, ethanol, various oils such as mineral oil, emulsions, and the like, or a solid vehicle, typically a powder, such as sucrose, mannose, trehalose, mannitol, bovine serum albumin, gelatin, pectins, Polyox®, polyvinylpyrrolidone, and the like. Typically, the solid formulations will be formed into dosage forms, such as tablets; elongated tablets; capsules; caplets; spheres; pellets; elementary osmotic pumps, such as those described in U.S. Pat. No. 3,845,770; mini-osmotic pumps, such as those described in U.S. Pat. Nos. 3,995,631, 4,034,756, and 4,111,202; and multichamber osmotic systems referred to as push-pull and push-melt osmotic pumps, such as those described in U.S. Pat. Nos. 4,320,759 and 4,449,983; all of the above patents of which are incorporated herein by reference; and the like. The various formulations may be delivered by devices designed to release the formulations at a particular and controlled time and in particular locations in the gastrointestinal tract, examples of such delivery devices being the CHRONSET™ delivery device (ALZA Corporation) and the Pulsincap™ device (R.P. Scherer & Co.). A wide variety of such oral dosage forms exists and are amply described in the medical and patent literature. See, for example, Remington's *Pharmaceutical Sciences*, Mack Publishing Co., Easton, Pa., 16th Edition, 1982, the disclosure of which is incorporated herein by reference.

By "pharmaceutically effective", it is meant that a sufficient amount of the active agent will be present in the carrier particle to provide for a desired therapeutic, prophylactic, or other biological effect or response when the compositions are administered to a host in any of the single dosage forms described above. The particular amount of active agent in any dosage will vary widely according to the nature of the active agent, the nature of the condition being treated, the age and size of the host, and the like. Generally, the amount of active agent in the pharmaceutical composition will vary from less than about 0.1% by weight to about 20% by weight of the composition, or more. The single dosage may vary from about 0.01 μg to 10 mg of the active agent per kilogram of body weight of the host, with dosages from about 0.1 μg to 1 mg/kg being commonly employed. These concentrations, however, are general guidelines only and particular amounts and dosages may be selected based on the active agent being administered, the condition being treated, and the treatment regimen being employed.

The pharmaceutical compositions of the present invention will be administered orally to the mammalian host, usually a human patient, according to a schedule which depends on the disease or condition being treated. In the case of acute diseases and conditions, it will often be necessary to administer one or more dosages on a daily basis over a relatively short timespan, such as days, weeks, or months. In the case of chronic diseases or conditions, it will often be necessary to administer the drug over a much longer time period, typically on a daily basis for an indefinite time.

The following examples are offered by way of illustration and not by way of limitation.

EXAMPLE 1

To 20 mg of polyisobutylcyanoacrylate particles with insulin encapsulated (following the procedures of Damage et al., J. Contr. Rel. 13, 233–239, 1990) and suspended in 5 mL of 50 mM sodium bicarbonate, pH 9.0, a 0.2 mL solution of acetonitrile containing 10 mmoles of 6-aminohexanoic acid is added. The mixture is incubated for 2 hr at RT. The hexanoic acid-modified particles are separated from the mixture by centrifugation at 20,000 g for 30 min and washed with the sodium bicarbonate buffer. The particles are resuspended in 5 mL of water. To the particle solution are added 10 mmoles of Arg-Gly-β-p-nitrophenyl-Asp p-nitrophenyl ester, and 10 mmoles of 1-hydroxybenzotriazole in 5 mL of DMF:water (1:1) are added to the solution. While slowly stirring, 10 mmoles of 1-cyclohexyl-3(2-morpholinoethyl) carbodiimide in 5 mL of water are added, and the mixture is then incubated for 2 hr at RT. At the end of the incubation, the pH of the solution is adjusted to 9.0 and further incubated for 2 hr. The particles with Arg-Gly-Asp attached to the polymer are then separated by centrifugation as above and washed with 50 mM sodium phosphate, pH 7.0.

EXAMPLE 2

Carboxylate-modified latex particles are commercially available, e.g., from Seragen Diagnostics, Inc., Indianapolis, Ind. Molecules of EGF are covalently attached to the latex particles as follows. To 12 mg of the carboxylate-modified latex in 1 mL of water are added 1.2 mg of N-hydroxybenzotriazole (in 0.5 mL of 50% DMF) and 3.5 mg of 1-cyclohexyl-3-(2-morpholinoethyl)carbodiimide in 0.5 mL of water while the particles are well stirred at RT. After 1 hr of stirring, the particles are centrifuged at 20,000 g for 20 min, washed with 0.1M NaCl. To this activated latex in 1 mL of 0.1M NaCl, 1 mL of EGF solution (5 mg/mL in water) is added. The solution is stirred overnight at 5° C. The conjugate of EGF and latex is separated by centrifugation as above and resuspended in 1 mL of 50 mM sodium phosphate buffer, pH 7.0. A solution of protein drug such as 1 mL of 1 mg/mL insulin is added to the latex particles and incubated overnight at 5° C. The insulin-adsorbed particles with covalently bound EGF are then purified by centrifugation as described in Example 1.

EXAMPLE 3

Nanoparticle Delivery of Insulin by the Integrin Pathway

Nanoparticles of polyisobutylcyanoacrylate containing 1 unit of insulin/mg are prepared as described by Michel et al. (supra). The preparation is purified by centrifugation and repeated washings in phosphate (0.02M) buffered saline (PBS) at pH 7. The resulting preparation is lyophilized, and 100 mg are then suspended in 2 mL of PBS to give the control particles, without a binding moiety (preparation A).

One mL of the above suspension of nanoparticles is added to 200 µg of Peptite-2000™ (Telios), containing the RGD tripeptide. The solution is incubated for 4 hr at room temperature. The particles are then centrifuged repeatedly from a suspension in PBS to give insulin-encapsulated polyisobutylcyanoacrylate particles modified by the adsorption of RGD peptide, which forms strong non-covalent bonds with the surface of the nanoparticles. The final solution is adjusted to contain 10 mg/mL of nanoparticles bound to the RGD binding moiety according to the present invention, representing 10 units of insulin per mL solution (preparation B).

The control preparation A is adjusted to the same concentration of insulin and nanoparticles as preparation B.

Diabetic rats are prepared by injection of 65 mg/kg body weight of streptozotocin. The rats each receive 10 units of insulin in the format of preparation A (the control) or preparation B (the RGD-treated material). Blood glucose levels are determined daily.

In the control, diabetic glucose levels return to normal from day 2 to day 4, returning to diabetic levels on day 6. In the animals receiving preparation B, glucose levels return to normal on day 2 and remain normal until day 6, returning to diabetic levels on day 9.

Although the foregoing invention has been described in detail for purposes of clarity of understanding, it will be obvious that certain modifications may be practiced within the scope of the appended claims.

What is claimed is:

1. A method for systemically delivering a protein or polypeptide drug to a mammalian host, said method comprising (a) orally administering to the host a composition which comprises the protein or polypeptide drug protectively retained by a carrier particle wherein said carrier particle is attached to a binding moiety which binds specifically to a target molecule present on the surface of a mammalian enterocyte, the target molecule being an endocytosis- or phagocytosis- promoting receptor, and (b) delivering the protein or polypeptide drug through the intestinal mucosa of the host to the blood stream of the host, wherein the carrier particle is absorbed by the mammalian enterocyte prior to release of the protein or polypeptide drug from the particle.

2. A method as in claim 1, wherein the active agent is a polypeptide drug.

3. A method as in claim 1, wherein the carrier particle is a nanoparticle.

4. A method as in claim 1, wherein the binding moiety is an adhesion molecule or a mimic thereof, or a fragment of an adhesion molecule or a mimic thereof.

5. A method as in claim 1, wherein the binding moiety is selected from the group consisting of an oligopeptide containing the sequence RGD, an invasin molecule or a fragment thereof, EGF or a fragment thereof, and an antibody or a fragment thereof.

* * * * *